(12) United States Patent
Tokii

(10) Patent No.: US 8,233,288 B2
(45) Date of Patent: Jul. 31, 2012

(54) ELECTRONIC COMPONENT PACKAGE, ELECTRONIC COMPONENT MOUNTED APPARATUS, METHOD OF INSPECTING BONDING PORTION THEREIN, AND CIRCUIT BOARD

(75) Inventor: Seiji Tokii, Hyogo (JP)

(73) Assignee: Panasonic Corporation, Osaka (JP)

( * ) Notice: Subject to any disclaimer, the term of this patent is extended or adjusted under 35 U.S.C. 154(b) by 840 days.

(21) Appl. No.: 12/107,454

(22) Filed: Apr. 22, 2008

(65) Prior Publication Data

US 2008/0266825 A1    Oct. 30, 2008

(30) Foreign Application Priority Data

Apr. 24, 2007    (JP) ................................. 2007-113721
Mar. 7, 2008     (JP) ................................. 2008-058263

(51) Int. Cl.
   *H01R 9/00*    (2006.01)
(52) U.S. Cl. ........ 361/772; 361/761; 257/772; 257/737; 174/255
(58) Field of Classification Search .................. 361/772, 361/761; 174/255; 257/737, 772
See application file for complete search history.

(56) References Cited

U.S. PATENT DOCUMENTS

| | | | | |
|---|---|---|---|---|
| 7,064,015 B2 * | 6/2006 | Azuma | .......................... | 438/125 |
| 7,637,413 B2 * | 12/2009 | Hiramatsu et al. | ............ | 228/103 |
| 2001/0054753 A1 | 12/2001 | Oya | | |
| 2005/0167154 A1 | 8/2005 | Urano | | |

FOREIGN PATENT DOCUMENTS

| | | |
|---|---|---|
| JP | 8-274213 | 10/1996 |
| JP | 10-335796 | 12/1998 |
| JP | 11-297889 | 10/1999 |
| JP | 2006-024858 | 1/2006 |
| JP | 2007-005452 | 1/2007 |
| WO | 03/098983 | 11/2003 |

* cited by examiner

*Primary Examiner* — Yuriy Semenenko
*Assistant Examiner* — Andargie M Aychillhum
(74) *Attorney, Agent, or Firm* — Hamre, Schumann, Mueller & Larson, P.C.

(57) ABSTRACT

An electronic component package includes: an insulating carrier substrate; a connection wiring that is provided on one side of the carrier substrate; an IC chip that is connected to the connection wiring; an external connection land that is disposed on the other side of the carrier substrate and is connected to the connection wiring via a wiring in the carrier substrate; and a solder ball that is disposed on the external connection land. A region of the external connection land that can be bonded to the solder ball has an outer shape that includes at least one arc portion and at least one straight portion. With this configuration, it is possible to provide an electronic component mounted apparatus in which bonding failure of the external connection land and the circuit board-side land with the solder ball can be reduced, and the bonding state can be easily inspected, and a method of inspecting a bonding portion therein.

15 Claims, 13 Drawing Sheets b1 b2 b3 b4 b5

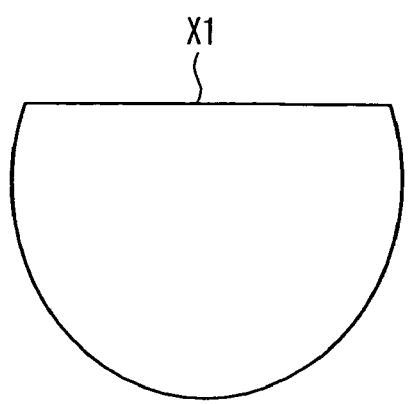
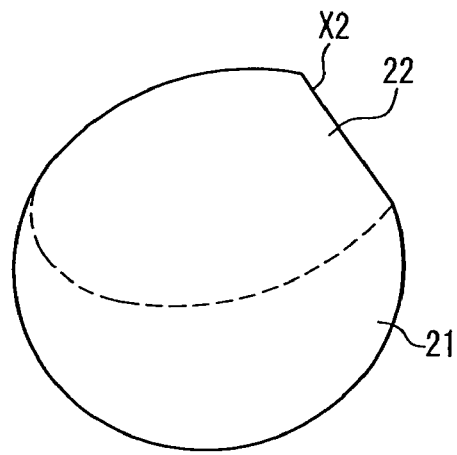
FIG. 5A    FIG. 5B
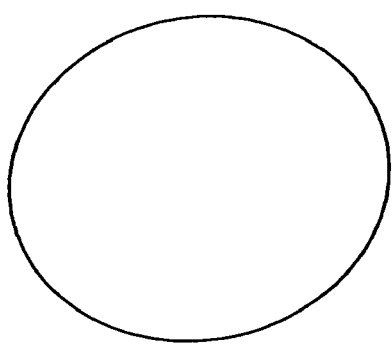
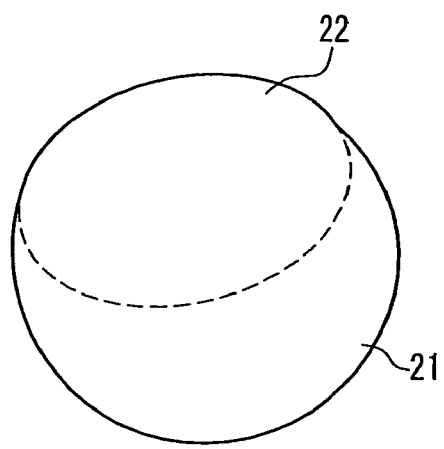
FIG. 5C    FIG. 5D
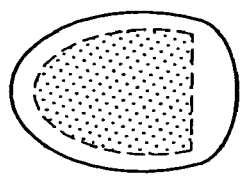
FIG. 6

ELECTRONIC COMPONENT PACKAGE, ELECTRONIC COMPONENT MOUNTED APPARATUS, METHOD OF INSPECTING BONDING PORTION THEREIN, AND CIRCUIT BOARD

BACKGROUND OF THE INVENTION

1. Field of the Invention

The present invention relates to a surface-mount type electronic component package in which an electronic component such as an IC is mounted, a circuit board, an electronic component mounted apparatus, and a method of inspecting a bonding portion therein.

2. Description of Related Art

Recently, as electronic equipment becomes smaller in size and more advanced in functionality, area array type IC packaging in which solder lands are provided on the bottom, such as BGA (Ball Grid Array) type and LGA (Land Grid Array) type CSP (Chip Size Packaging), is used widely to mount electronic components.

FIG. 17 is an enlarged cross-sectional conceptual diagram of a bonding portion of a conventional electronic component mounted apparatus in which a BGA package is mounted on a circuit board by soldering. The electronic component mounted apparatus 101 includes a BGA package (hereinafter referred to as an "electronic component package") 103 mounted on a circuit board 102. The circuit board 102 includes circuit board-side lands 106 that are disposed on an insulating substrate 105, and a part of which is covered with a circuit board-side resist 110.

The electronic component package 103 includes a carrier substrate 107, an IC chip (not shown) that is disposed on the upper surface 107a of the carrier substrate 107, external connection lands 108 that are disposed on the lower surface 107b of the carrier substrate, and a part of which is covered with a resist 111, and solder balls 104 that are disposed on the external connection land 108. The solder balls 104 connect the circuit board-side lands 106 and the external connection lands 108.

A method of manufacturing an electronic component mounted apparatus 101 with this configuration will be described next. First, an IC chip is mounted on the upper surface 107a of an insulating carrier substrate. Next, solder balls 104 are bonded to external connection lands 108 to form an electronic component package 103. A cream solder (not shown) is then applied onto circuit board-side lands 106. The external connection lands 108 and the circuit board-side lands 106 are positioned such that they face each other, and the solder balls are bonded to form bonding portions 109. An electronic component mounted apparatus 101 is manufactured through the above-described steps.

FIG. 18 shows cross sections i1 to i5 that are obtained by slicing a bonding portion 109 of FIG. 17 at slicing planes I1 to I5. Cross section i1 is the shape of the external connection land 107 that is free from the resist 111. Cross section i5 is the shape of the circuit board-side land 106 that is free from the resist 110.

Ordinarily, the cross sections i1 and i5 have a circular shape. Cross section i2 is slightly larger than cross section i1, and cross section i3 is the maximum cross-sectional region of the molten solder ball, which is the largest in size. Similarly, cross section i4 is slightly larger than cross section i5.

However, if the solder ball 104 and the external connection land 108 do not wet, the cross sectional shape increases discontinuously, irregularly, or the cross section i2 may be too small, rather than increasing almost continuously from cross sections i1 to i2. This phenomenon is difficult to detect by external visual inspection.

This defective solder wetting is caused by warping of the substrate due to heat generated during reflowing, weak activity of flux, random variations in solder ball size, or the like. If the solder ball has poor wettability, the bonding between the circuit board-side land and the external connection land will be defective.

As shown in FIG. 17, X-rays (direction of arrow) are irradiated from the upper side to the lower side in the diagram, and received by an X-ray-receiving apparatus (not shown) located in the lower side to create X-ray image data, and an X-ray image is displayed. The density is almost uniform within the shape of the smaller of the slicing planes I1 and I5, but the number of X-rays increases gradually toward the outer side. When this is expressed in X-ray image density, the density becomes gradually lighter from the inside toward the outside. However, in this configuration, the cross sections i1 and i2 cannot be distinguished, and it is therefore difficult to determine the acceptability of the wettability.

Further, because the transmission cross sections of the land and the solder ball have a similar circular shape, the boundary or contour of each shape does not appear clearly in X-ray image density, and it is therefore further difficult to distinguish the cross sections i1 and i2.

Also, because the solder ball is spherical and the land is circular, an X-ray image is displayed in the shape of a circle regardless of whether or not the solder ball wets and spreads, and it is therefore difficult to determine the acceptability of wettability (bondability with the land).

As a method of solving the above problem, an electronic component mounted apparatus has been disclosed in which circuit board-side lands are provided with a polygonal shape such as a quadrilateral shape (see, for example, JP H10-335796A).

With this configuration, if a solder ball has satisfactory wettability, the shape of the circuit board-side solder ball conforms to that of the land, and thus the X-ray image of the solder ball will not be circular. Based on this, it is possible to determine the acceptability of bondability of the bonding portion. Because the bondability can be determined nondestructively, the reliability of circuit boards and electronic circuit apparatuses can be increased.

Another technique has been disclosed in which a ceramic substrate is used as a chip carrier, and external connection lands are formed on the underside of the chip carrier, which are square in shape (see, for example, JP H8-274213A). This increases the connection area of a land with the carrier substrate. It is therefore possible to form an electronic component package in which the lands have a strong bonding strength.

Ordinarily, a molten solder ball to be bonded tends to form a circular shape due to surface tension, so that in a land configured as above, the straight portions are unlikely to be wetted with solder. Further, because the land has no arc portion (a portion of the perimeter of the land that has an arc shape), if one of the straight portions (portions of the perimeter of the land that are linear) of the land shape is not wetted with solder, the periphery of the other straight portions are unlikely to be wetted with solder, and the shape of the molten solder ball will be deformed considerably. This results in the problem that the occurrence of bonding failures between the circuit board-side land and the solder ball increases, and connection reliability is degraded.

SUMMARY OF THE INVENTION

Therefore, with the foregoing in mind, it is an object of the present invention to provide an electronic component mounted apparatus in which bonding failures between external connection lands and solder balls and between circuit board-side lands and the solder balls can be reduced, and the bonding state can be inspected easily, and a method of inspecting a bonding portion therein.

An electronic component package of the present invention includes an insulating carrier substrate, a connection wiring that is provided on one side of the carrier substrate, an IC chip that is connected to the connection wiring, an external connection land that is disposed on the other side of the carrier substrate and is connected to the connection wiring via a wiring in the carrier substrate, and a solder ball that is disposed on the external connection land. In order to solve the above problem, a region of the external connection land that can be bonded to the solder ball has an outer shape that includes at least one arc portion and at least one straight portion.

With this configuration, because the external connection land includes an arc portion, the molten solder ball that tends to form a circular shape due to surface tension wets without being deformed considerably, and therefore satisfactory bondability between the solder ball and the external connection land is obtained. Further, because the external connection land also includes a straight portion, the straight portion is displayed in an X-ray image, and the bondability between the solder ball and the external connection land can be inspected easily using X-rays. For this reason, the reliability of the bondability between the solder ball and the external connection land is improved.

A circuit board of the present invention includes an insulating substrate, a circuit board-side land that is disposed on the insulating substrate, and a wiring that is provided on the insulating substrate and is connected to the circuit board-side land. In order to solve the above problem, a region of the circuit board-side land that can be bonded to a solder ball of an electronic component package to be mounted has an outer shape that includes at least one arc portion and at least one straight portion.

With this configuration, because the circuit board-side land includes an arc portion, the solder ball of an electronic component package to be mounted wets without being deformed considerably, and satisfactory bondability between the solder ball and the circuit board-side land is obtained. Further, because the circuit board-side land also includes a straight portion, the straight portion is displayed in an X-ray image, and the bondability between the solder ball and the circuit board-side land can be inspected easily using X-rays. For this reason, the reliability of the bondability between the solder ball and the circuit board-side land is improved.

An electronic component mounted apparatus of the present invention includes the above-described electronic component package and above-described circuit board, wherein the solder ball is connected to the circuit board-side land. With this configuration, satisfactory bondability between the solder ball and the external connection land, and satisfactory bondability between the solder ball and the circuit board-side land are obtained. At the same time, the bondability between the solder ball and the external connection land and the bondability between the solder ball and the circuit board-side land can be inspected easily using X-rays.

A method of inspecting a bonding portion of an electronic component package of the present invention is a method of inspecting the bonding portion between the external connection land and the solder ball in the above-described electronic component package, wherein X-rays are irradiated on the solder ball and it is determined that the bonding portion between the external connection land and the solder ball in the electronic component package is satisfactory if a straight portion is included in the outer shape of the solder ball in an image formed based on X-rays that have passed through the solder ball. According to this method, the bonding state of the bonding portion between the external connection land and the solder ball can be determined easily by the presence of a straight portion of the external connection land.

A method of inspecting a bonding portion of an electronic component mounted apparatus is a method of inspecting the bonding portion between the external connection land and the circuit board-side land by the solder ball in the above-described electronic component mounted apparatus, wherein X-rays are irradiated on the solder ball and it is determined that at least one of the bonding portion between the external connection land of the electronic component package and the solder ball and the bonding portion between the circuit board-side land of the circuit board and the solder ball is satisfactory if a straight portion is included in the outer shape of the solder ball in an image formed based on X-rays that have passed through the solder ball. According to this method, the bonding state of the bonding portion between the external connection land and the solder ball can be determined easily. According to this method, the bonding state of the bonding portion between the external connection land and the circuit board-side land by the solder ball can be determined easily by the presence of a straight portion of the external connection land and the circuit board-side land.

BRIEF DESCRIPTION OF THE DRAWINGS

FIG. 5A is a conceptual diagram of an X-ray image of a bonding portion of an electronic component mounted apparatus in which an electronic component package is solder-bonded according to Embodiment 1 of the present invention.

FIG. 5B is a conceptual diagram of an X-ray image of a bonding portion of an electronic component mounted apparatus in which electronic component package is solder-bonded according to Embodiment 1 of the present invention.

FIG. 5C is a conceptual diagram of an X-ray image of a bonding portion of an electronic component mounted apparatus in which electronic component package is solder-bonded according to Embodiment 1 of the present invention.

FIG. 5D is a conceptual diagram of an X-ray image of a bonding portion of an electronic component mounted apparatus in which electronic component package is solder-bonded according to Embodiment 1 of the present invention.

FIG. 6 is a conceptual diagram of an X-ray image of a bonding portion of an electronic component mounted apparatus in which electronic component package is solder-bonded according to Embodiment 1 of the present invention.

DESCRIPTION OF THE PREFERRED EMBODIMENTS

Figure 1A:
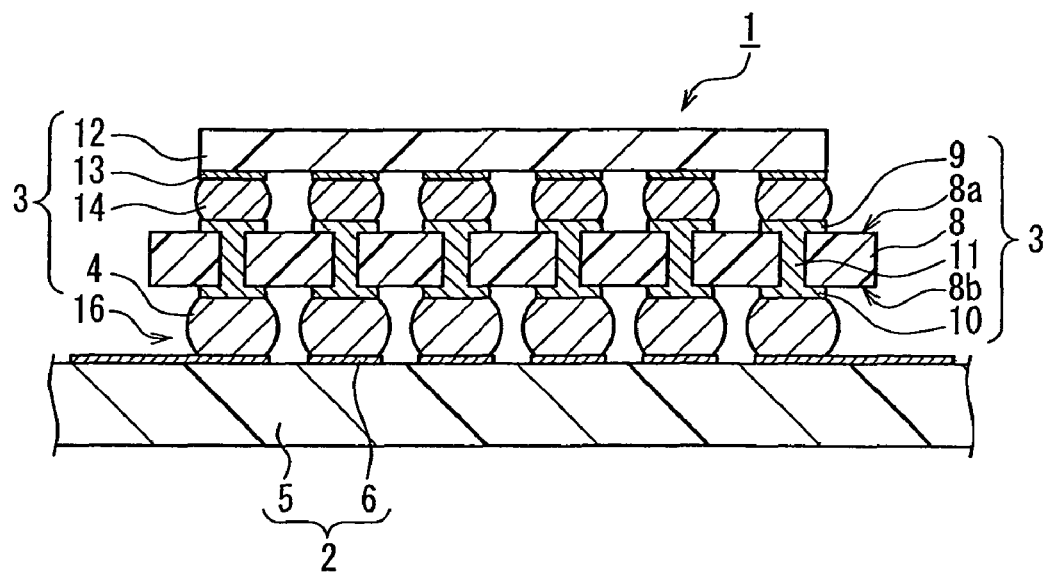
FIG. 1A is a cross-sectional conceptual diagram illustrating the configuration of an electronic component mounted apparatus that includes an electronic component package according to Embodiment 1 of the present invention.

In the electronic component package, circuit board, and electronic component mounted apparatus according to the present invention, a land includes an arc portion and a straight portion. With this configuration, it is possible to obtain satisfactory bondability between a solder ball and the land. At the same time, the bondability between the solder ball and the land can be inspected easily using X-rays.

The present invention can have various embodiments based on the above-described configuration. Specifically, in an electronic package as described above, the entire surface of the external connection land can constitute a region that can be bonded to the solder ball.

It is also possible to adopt a configuration in which a resist that is disposed on the other side of the carrier substrate and has an opening is provided, and a region of the external connection land that is exposed through the opening of the resist is the region that is to be bonded to the solder ball.

The region of the external connection land that can be bonded to the solder ball also can be configured to have an outer shape that includes a substantially semicircular arc portion and a straight portion that connects two ends of the arc portion. With this configuration, the external connection land includes one straight portion, which makes it easy to identify the arc portion and the straight portion in an X-ray image.

The region of the external connection land that can be bonded to the solder ball can also be configured to have an outer shape that includes a plurality of arc portions and a plurality of straight portions, each of the straight portions connecting one end of an arc portion and one end of another arc portion. With this configuration, the straight portions can be viewed regardless of the X-ray irradiation direction, and therefore the bonding state can be determined in a short time.

The circuit board of the present invention can be configured such that the entire surface of the circuit board-side land is the region that can be bonded to a solder ball of an electronic component package to be mounted.

It is also possible to adopt a configuration in which a resist that is disposed on the insulating substrate and has an opening is provided, and a region of the circuit board-side land that is exposed through the opening of the resist is the region that can be bonded to the solder ball of the electronic component package to be mounted.

The region of the circuit board-side land that can be bonded to the solder ball of the electronic component package to be mounted can be configured to have an outer shape that includes a substantially semicircular arc portion and a straight portion that connects two ends of the arc portion. With this configuration, the circuit board-side land includes one straight portion, and it is therefore easy to distinguish the arc portion from the straight portion in an X-ray image.

The region of the circuit board-side land that can be bonded to a solder ball of an electronic component package to be mounted can be configured to have an outer shape that includes a plurality of arc portions and a plurality of straight portions, each of the straight portions connecting one end of an arc portion and one end of another arc portion. With this configuration, the straight portions can be viewed regardless of the X-ray irradiation direction, and therefore the bonding state can be determined in a short time.

In the method of inspecting a bonding portion of an electronic component package of the present invention, the X-rays may be irradiated obliquely relative to the plane of the carrier substrate of the electronic component package. With this configuration, a straight portion can be viewed no matter where it is located, and thus the bonding state can be determined in a short time.

In the method of inspecting a bonding portion of an electronic component mounted apparatus of the present invention, the X-rays may be irradiated obliquely relative to the plane of the carrier substrate of the electronic component package. With this configuration, a straight portion can be viewed no matter where it is located, and thus the bonding state can be determined in a short time.

Hereinafter, embodiments of the present invention will be described with reference to the accompanying drawings.

Embodiment 1

Figure 1B:
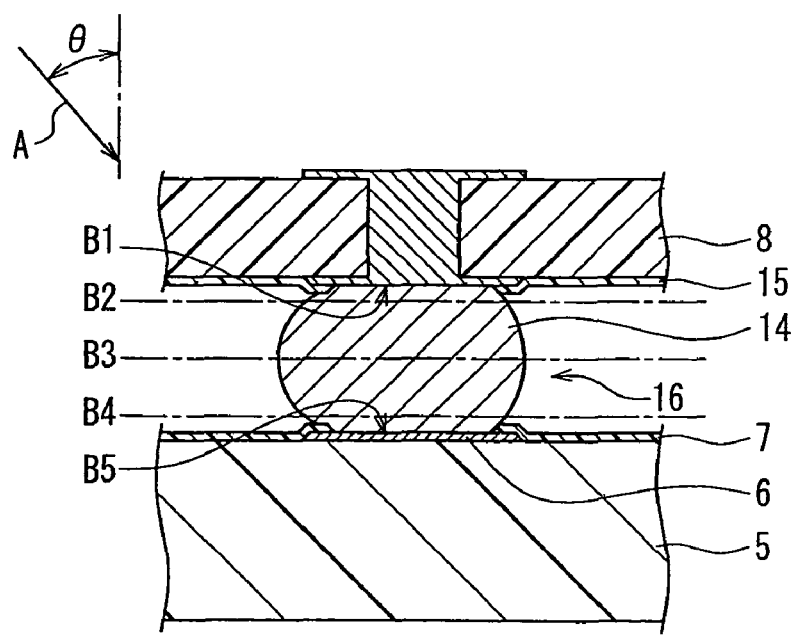
FIG. 1B is an enlarged cross-sectional conceptual diagram showing a relevant part of FIG. 1A.
Figure 2A:
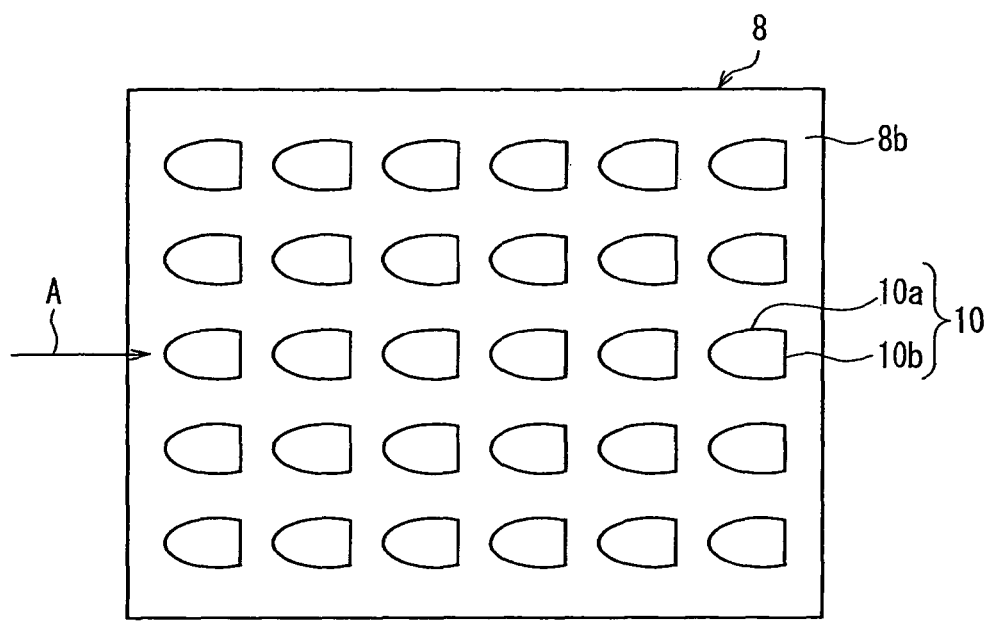
FIG. 2A is a conceptual diagram of the lower surface of a carrier substrate according to Embodiment 1 of the present invention.
Figure 2B:
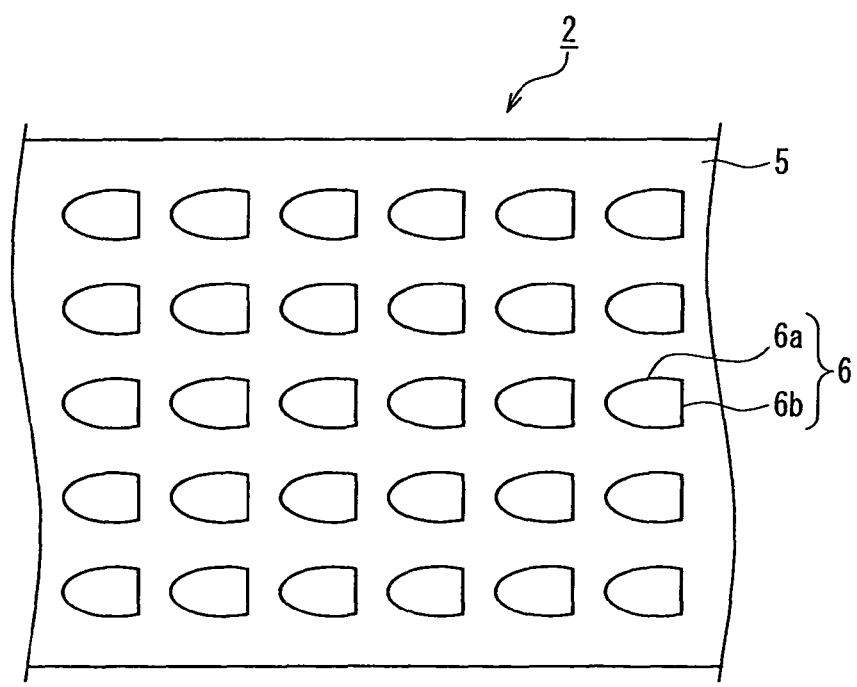
FIG. 2B is a conceptual diagram of a circuit board according to Embodiment 1 of the present invention.

FIG. 1A is a cross-sectional conceptual diagram illustrating the configuration of an electronic component mounted apparatus 1 that includes an electronic component package 3 according to Embodiment 1 of the present invention. FIG. 1B is an enlarged cross-sectional conceptual diagram showing a part of FIG. 1A. The same reference numerals are assigned to elements having the same configuration, and some of the reference numerals are omitted. FIG. 2A is a conceptual diagram of the lower surface 8b of a carrier substrate according to the present embodiment. FIG. 2B is a conceptual diagram of a circuit board 2 according to the present embodiment. In FIGS. 2A and 2B, the same reference numerals are assigned to elements having the same configuration as those of FIGS. 1A and 1B, and some of the reference numerals are omitted.

As shown in FIG. 1A, the electronic component mounted apparatus 1 includes an electronic component package 3 mounted on a circuit board 2. The electronic component package 3 includes an IC chip 12 mounted on an upper surface 8a of a carrier substrate 8, and solder balls 4 disposed on a lower surface 8b of the carrier substrate 8.

The carrier substrate 8 is composed of an insulating material. As the insulating material of the carrier substrate 8, materials obtained by impregnating a glass fiber or a fiber made of an organic material such as Kevlar, with an epoxy resin, phenol resin, polyimide resin or the like and curing the resultant, materials in which a BT resin is used, and the like can be used. Besides substrates made of resin, an insulating ceramic substrate can be used.

Connection wirings 9 are disposed on the upper surface 8a of the carrier substrate. The connection wirings 9 are formed by pattern printing a wiring pattern-forming conductive paste that includes, for example, copper particles by screen printing. On the lower surface 8b of the carrier substrate, external connection lands 10 are disposed. As shown in FIG. 1B, a resist 15 covers a part of each external connection land 10 formed on the lower surface 8b of the carrier substrate, and has an opening at the position of the external connection land 10. The shape of the exposed external connection land 10 is defined by the shape of the opening.

As shown in FIG. 1A, via holes 11 formed in the carrier substrate 8 connect the connection wirings 9 and the external connection lands 10. The via holes 11 are formed by filling a through hole of the carrier substrate 8 with a conductive paste, for example, when the screen printing is performed.

Electrode bumps 13 made of gold (Au) are disposed on the IC chip 12. The IC chip 12 is mounted on the carrier substrate 8 with the surface side (the side on which the electrode bumps 13 are formed) facing down. The bonding portions between the electrode bumps 13 and the connection wirings 9 are sealed with a sealant (not shown). Solder balls 14 connect the electrode bumps 13 and the connection wirings 9.

The circuit board 2 includes circuit board-side lands 6 formed on an insulating substrate 5. As the circuit board 2, a printed circuit board can be used. As shown in FIG. 1B, a resist 7 covers a part of each circuit board-side land 6 formed on the insulating substrate 5, and has an opening in the position of the circuit board-side land 6. The shape of the circuit board-side land 6 is defined by the shape of the opening. The external connection lands 10 and the circuit board-side lands 6 are disposed in such a position that they face each other, and they are connected via the solder balls 14.

In the present embodiment, the shape of the external connection lands 10 or that of the openings of the resist 15 is a shape that includes at least one arc portion and at least one straight portion. Specifically, as shown in FIG. 2A, the external connection lands 10 have a substantially semicircular shape that includes an elliptic arc portion 10a and a straight portion 10b that connects two ends of the elliptic arc portion 10a. In this case, the substantially semicircular shape may be the shape of the external connection lands 10 or the shape defined by the shape of the openings of the resist 15 shown in FIG. 1B. In either case, similar effects can be obtained.

The shape of the circuit board-side lands 6 or that of the openings of the resist 7 (see FIG. 1B) is a shape that includes at least one arc portion and at least one straight portion. As shown in FIG. 2B, the circuit board-side lands 6 have a substantially semicircular shape that includes an elliptic arc portion 6a and a straight portion 6b that connects two ends of the elliptic arc portion 6a. In this case, the substantially semicircular shape may be the shape of the circuit board-side lands 6 or the shape defined by the shape of the openings of the resist 7 shown in FIG. 1B. In either case, similar effects can be obtained.

The process of mounting the electronic component package 3 onto the circuit board 2 will be described next. First, the circuit board 2 and the electronic component package 3 are positioned such that the circuit board-side lands 6 and the external connection lands 10 face each other. Then, the electronic component package 3 on which an IC chip 12 is already mounted via solder balls 4 is placed on the circuit board 2. The resultant is then subjected to reflow in a furnace to cause the circuit board-side lands 6 and the external connection lands 10 to metal-bond by the solder balls 4, forming bonding portions 16. The electronic component package 3 is mounted on the circuit board 2 in this manner to manufacture the electronic component mounted apparatus 1.

Because the external connection lands 10 have a substantially semicircular shape including an elliptic arc portion 10a and a straight portion 10b that connects the two ends of the elliptic arc portion 10a, molten solder balls that tend to form a circular shape due to surface tension during reflowing wet in the elliptic arc portion 10a without being deformed considerably, and the straight portion 10b is also wetted. In other words, all of the external connection land 10 is wetted, and thus a boding portion 16 having satisfactory bonding is formed. Consequently, the occurrence of bonding failures between the external connection lands 10 and the solder balls 4 can be reduced, and thus connection reliability is improved.

Similarly, because the circuit board-side land 6 also has a substantially semicircular shape including an elliptic arc portion and a straight portion that connects two ends of the elliptic arc portion, the occurrence of bonding failures between the circuit board-side lands 6 and the solder balls 4 can be reduced, and thus connection reliability is improved.

In the foregoing, a case where the arc portion is an elliptic arc portion has been described, but the arc portion may have a circular arc shape, an elliptic arc shape, or a combination thereof as long as the arc shape has a moderate curvature. In the case where a land includes one arc portion and one straight portion that connects two ends of the arc portion, the land has a substantially semicircular shape.

Figure 3A:
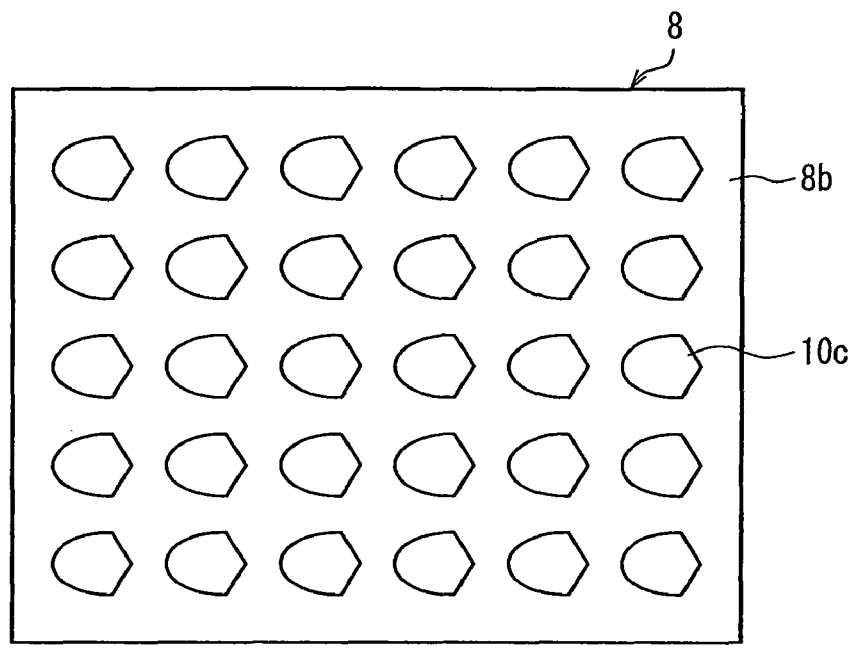
FIG. 3A is a conceptual diagram of the lower surface of another carrier substrate according to Embodiment 1 of the present invention.
Figure 3B:
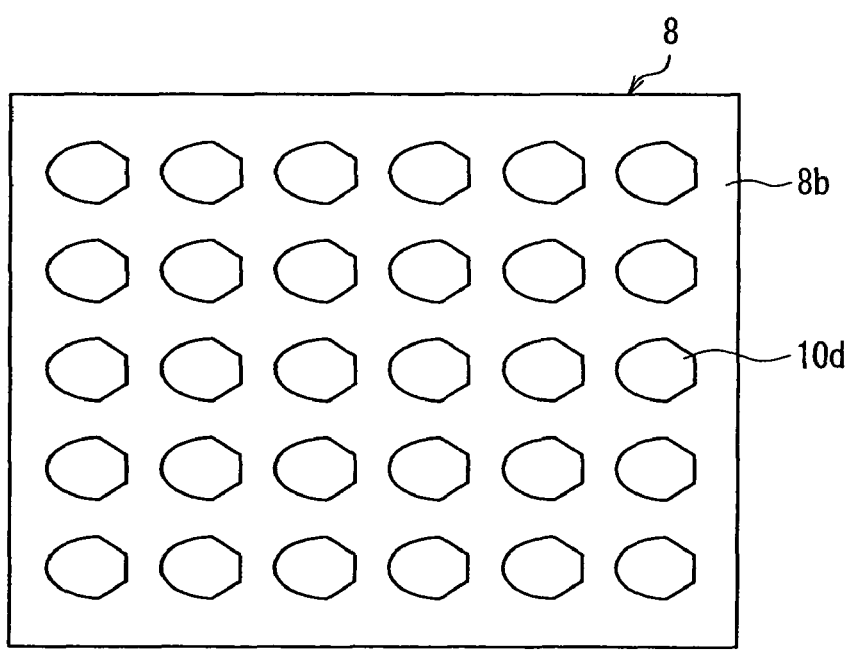
FIG. 3B is a conceptual diagram of the lower surface of another carrier substrate according to Embodiment 1 of the present invention.

In the foregoing, a case where the external connection lands 10 are provided to have a substantially semicircular shape that includes one arc portion and one straight portion has been described, but it is also possible to provide, for example, external connection lands 10c having a shape that includes an arc portion and two straight portions connecting two ends of the art portion as shown in FIG. 3A on the lower surface 8b of the carrier substrate 8. Alternatively, as shown in FIG. 3B, external connection lands 10d having a shape that includes one arc portion and three straight portions connecting two ends of the arc portion may be provided on the lower surface 8b of the carrier substrate 8. Alternatively, the external connection lands 10 may be configured to have a shape that includes one arc portion and four or more straight portions connecting two ends of the arc portion. The external connection lands 10 may also be configured to have a shape that includes a plurality of arc portions and a plurality of straight portions that connect the arc portions.

In this case, it is desirable that the angle formed by a straight portion and an arc portion is obtuse. Thereby, a molten solder ball can easily wet between the two portions that form the obtuse angle, and therefore satisfactory bonding can be achieved. This also reduces the occurrence of bonding failure and improves connection reliability.

Similarly, the circuit board-side lands 6 also can have a shape where one arc portion connects at least one straight portion. This provides effects similar to the case of the external connection lands 10. The circuit board-side lands 6 also may have a shape that includes a plurality of arc portions and a plurality of straight portions that connect the arc portions. Thereby, the occurrence of bonding failure can be reduced in the circuit board-side lands 6, and thus connection reliability is improved.

Because the external connection lands 10 have a straight portion 10*b*, when inspecting a bonding portion by X-ray transmission, which will be described below, the contours of different shapes derived from the substantially semicircular shape of the solder ball's cross section and the land's straight portion 10*b* are shown in an X-ray image, which makes it easy to determine the acceptability of the bonding state.

Next, the process of inspecting the bonding state of a bonding portion 16 between the circuit board 2 and the electronic component package 3 of the electronic component mounted apparatus 1 of the present invention will be described next.

First, X-rays are irradiated to a bonding portion 16 of the electronic component mounted apparatus 1. Then, the X-rays that have passed through the bonding portion 16 are received by an X-ray receiving apparatus (not shown) to create image data, and a display apparatus (not shown) displays an X-ray image. The operator determines the acceptability of the bonding state of the bonding portion 16 based on the following criteria after observing the X-ray image. As the X-rays, for example, soft X-rays can be used. The transmittance of soft X-rays varies according to the solder thickness. In other words, when solder is thick, the amount of X-rays transmitted will be small. Conversely, when solder is thin, the amount of X-rays transmitted will be large, resulting in an X-ray image having variations in density due to the thickness of the solder.

Figure 4:
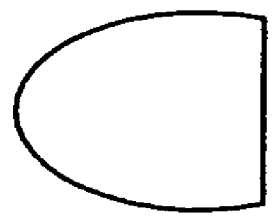
FIG. 4 is a cross-sectional conceptual diagram illustrating the cross sections of slicing planes B1 to B5 of FIG. 1B.
Figure 4:
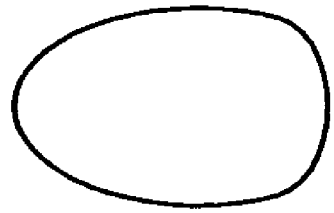
Figure 4:
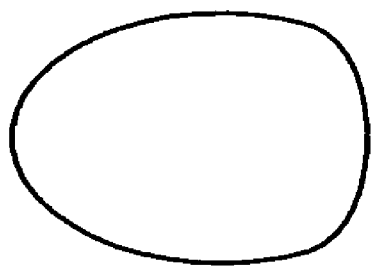
Figure 4:
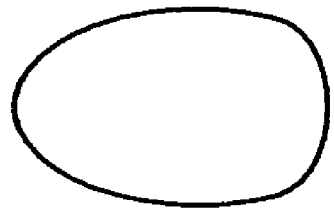
Figure 4:
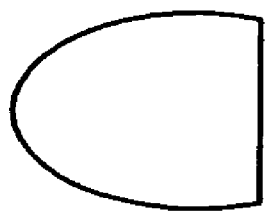

FIG. 4 is a cross-sectional conceptual diagram illustrating cross sections b1 to b5 obtained by slicing the bonding portion 16 of FIG. 1B at slicing planes B1 to B5. Slicing plane B1 is the surface of the external connection land 10, and cross section b1 shows the shape of the external connection land 10 (the shape of a portion thereof that is free from the resist 15). Likewise, slicing plane B5 is the surface of the circuit board-side land 6, and cross section b5 shows the shape of the circuit board-side land 6 (the shape of a portion thereof that is free from the resist 7).

Ordinarily, if solder is bonded well to a land as a result of good wetting and spreading of the solder, the shape of the boundary between the solder and the land resembles the shape of the land. Specifically, because the external connection lands 10 have a substantially semicircular shape as shown by the cross section b1 of FIG. 4, if soldering is done appropriately, the closer the slicing plane B2 is to the external connection land 10, the closer the shape of the cross section b2 becomes to a substantially semicircular shape (the shape of the external connection land 10) that is rounded.

If, on the other hand, solder is bonded poorly to a land due to poor wetting and spreading of the solder, the surface tension of the solder exceeds the wetting force of the solder on the land, and as a result, the solder ball is forced to have a small surface area, that is, to form a spherical shape, by the surface tension. Therefore, there is little correlation between the shape of the solder ball and that of the land.

Accordingly, if a solder ball 4 does not wet in the vicinity of an external connection land 10, or if diffusion and bonding is not performed appropriately, the cross section of the solder ball 4 at the slicing plane B2 will have a deformed substantially circular or elliptic shape, or an irregular and discontinuous shape.

An X-ray image of a bonding portion 16 will be described next. As shown in FIG. 4, cross section b3 has the largest area among the cross sections b1 to b5. Accordingly, when X-rays are irradiated from a direction perpendicular to the plane of the circuit board 2, the shape of cross section b3 is displayed in an X-ray image, and it is difficult to determine the bonding state. To avoid this, either one or both of an X-ray source and the electronic component mounted apparatus are moved at the desired angle, and a plurality of X-ray images are captured and image-processed.

In the present embodiment, X-rays are irradiated along the direction indicated by arrow A in FIGS. 1B and 2A at an angle of θ (e.g., about 40 degrees) relative to the line normal to the plane of the carrier substrate 8, and they are irradiated in a direction approximately orthogonal to the straight portion 10*b* of each external connection land 10 having a substantially semicircular shape.

FIGS. 5A to 5D schematically show X-ray images. FIGS. 5B and 5D are obtained through three-dimensional observation, in which observation is performed in a planar rotation angle in addition to an oblique direction (the abovementioned irradiation direction), that provides difference images that show a more clear difference and a connected state close to the actual state. In the solder ball images 21 shown in FIGS. 5B and 5D, the portion indicated by a broken line is a bonding portion image 22 that shows the shape of a bonding portion with an external connection land 10. FIGS. 5A and 5B illustrate a satisfactory bonding state of a bonding portion 16. In the case of satisfactory bonding, a straight portion can be viewed from any direction (θ is usually from 10 to 60 degrees) as indicated by X1 in FIG. 5A and X2 in FIG. 5B.

FIGS. 5C and 5D show defective bonding state of a bonding portion 16. In the case of defective bonding, if the X-ray irradiation angle is changed to a predetermined angle or greater, the straight portion (X1, X2) is curved as shown in FIGS. 5C and 5D, and no straight portion can be observed. Accordingly, it is possible to clearly distinguish defective solder connections from normal solder connections.

As shown in FIG. 5B, if a bonding portion image 22 that includes a clear contour of a straight portion appears in an X-ray image, it indicates that the solder ball 4 is wetted and bonded to the entire semicircular external connection land 10, and therefore the bonding is satisfactory. However, if a bonding portion image 22 that includes no contour of a straight portion as shown in FIG. 5D appears in an X-ray image, or if the bonding portion image 22 appears in a deformed substantially semicircular or deformed substantially elliptic shape, or in an irregular and discontinuous shape, and the like, it indicates that the solder ball is bonded only to a part of the substantially semicircular external connection land 10, and therefore the bonding is defective. In short, the operator can determine the bonding state based on the criteria that if a straight portion is observed in an X-ray image of a bonding portion 16, the bonding state is satisfactory, and if no straight portion is observed, the bonding state is defective.

In the foregoing, X-rays are irradiated obliquely at about 40 degrees relative to the line normal to the plane of the carrier substrate 8, but the irradiation angle and direction can be set such that the straight portion of the bonding portion image 22 can be viewed in an X-ray image. Alternatively, if the perimeter of a land includes a plurality of straight portions, by additionally setting the irradiation angle and direction, the inspection can be performed more easily.

As described above, because the external connection lands 10 have a shape including an arc portion and a straight portion, the contours of different shapes derived from the substantially semicircular shape of the solder ball's cross section and the straight portion are shown in an X-ray image, which makes it easy to inspect the bonding state. Further, because there is only one straight portion, it is possible to distinguish clearly the straight portion from the arc portion in an X-ray image, and thus the acceptability of the bonding can be determined more easily.

By irradiating X-rays from a predetermined oblique direction as described above, in the X-ray image of the vicinity of the straight portion of a land, a clear contour of a straight portion is shown, and thus the acceptability of the bonding can be determined more easily.

In the foregoing, the bonding state between a solder ball 4 and an external connection land 10 of the electronic component mounted apparatus 1 has been described, but the bonding state between a solder ball 4 and a circuit board-side land 6 also can be inspected in the same manner as that for the bonding state between a solder ball 4 and an external connection land 10. It is also possible to inspect both the bonding state between a solder ball 4 and an external connection land 10 and that between the solder ball 4 and a circuit board-side land 6.

The bonding state between a solder ball 4 and an external connection land 10 of an electronic component package 3 in which solder balls 4 are bonded to external connection lands 10 also can be inspected in the same manner as in the case of the electronic component mounted apparatus 1.

With any of the above-described methods of inspecting a bonding state, the bonding state between a land and a solder ball can be determined easily.

In the foregoing, a case where X-rays are irradiated obliquely relative to the electronic component package has been described, but X-rays also may be irradiated from a direction normal to the plane of the electronic component package. FIG. 6 is a conceptual diagram of an X-ray image illustrating an example of an (image-processed) X-ray transmission image of a bonding portion 16 of the electronic component mounted apparatus. If the bonding state of the bonding portion 16 is satisfactory, the portion of the external connection land 10 that is indicated by a broken line is displayed darkly. This is because the overlapping area of the substantially circular shape of the solder ball's cross section and the land's substantially semicircular shape including an elliptic arc portion and a straight portion appears dark. Accordingly, the bonding state can be inspected by whether or not a straight portion is observed.

In the present embodiment, a configuration has been described in which the via holes 11 are formed in the carrier substrate 8 so as to connect the connection wirings 9 formed on the upper surface 8a of the carrier substrate and the external connection lands 10 formed on the lower surface 8b of the carrier substrate. However, the present invention is not limited to via holes, and as long as wirings are formed in the carrier substrate 8, as for example in the case of a multilayer substrate.

In the present embodiment, the external connection lands have been described, but by adopting the same configuration in the circuit board-side lands as shown by the cross section b5 of FIG. 4, the occurrence of bonding failures with solder balls can be reduced, and connection reliability can be improved, and at the same time, bondability can be easily determined.

Further, FIG. 4 shows a configuration in which the straight portions of the external connection land and the circuit board-side land are formed in the same orientation from the center of each land, but they may be formed in different orientations. When the straight portions are formed in different orientations, they are displayed in different orientations in an X-ray image, and therefore if bonding failure occurs, it is possible to determine easily to which of the external connection land and the circuit board-side land the solder ball is poorly bonded.

Embodiment 2

Figure 7:
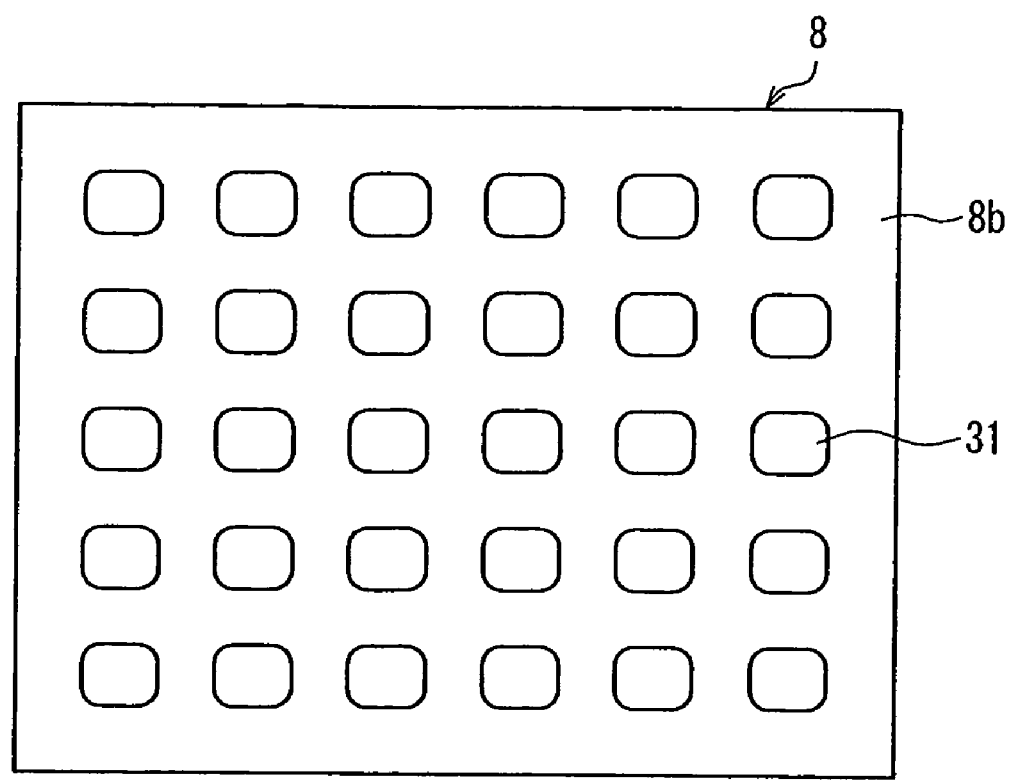
FIG. 7 is a conceptual diagram of the lower surface of a carrier substrate according to Embodiment 2 of the present invention.

FIG. 7 is a plan view illustrating the configuration of external connection lands 31 of a carrier substrate 8 of a semiconductor mounting apparatus according to Embodiment 2 of the present invention. The semiconductor mounting apparatus according to the present embodiment is the same as that of Embodiment 1, except that the external connection lands 31 have a configuration different from that of the external connection lands of Embodiment 1. In the semiconductor mounting apparatus of the present embodiment, the same reference numerals are assigned to elements having the same configuration as that of the semiconductor mounting apparatus of Embodiment 1, and thus their descriptions are omitted.

The external connection lands 31 have a rectangular shape whose corner portions are circular arc-shaped, that is, a shape that includes four arc portions and four straight portions that are connected to each other. With this configuration, molten solder balls 4, which tend to form a circular shape due to surface tension, wet uniformly in the four circular arc portions of the external connection lands 31 without being deformed, and thus the occurrence of bonding failures between the external connection lands 31 and the solder balls 4 can be reduced, and connection reliability can be improved.

Figure 8A:
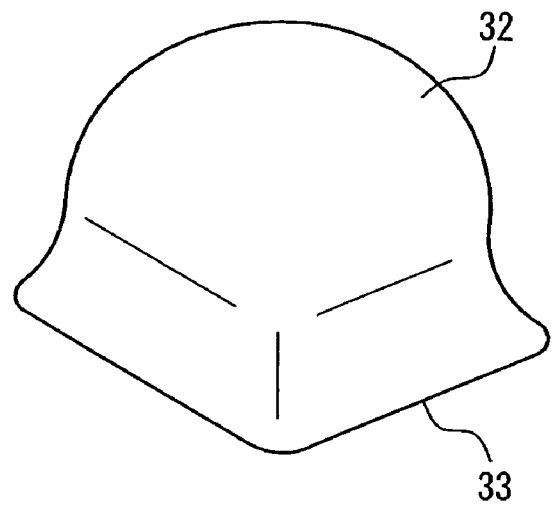
FIG. 8A is a schematic diagram illustrating an X-ray image of satisfactory bonding according to Embodiment 2 of the present invention.
Figure 8B:
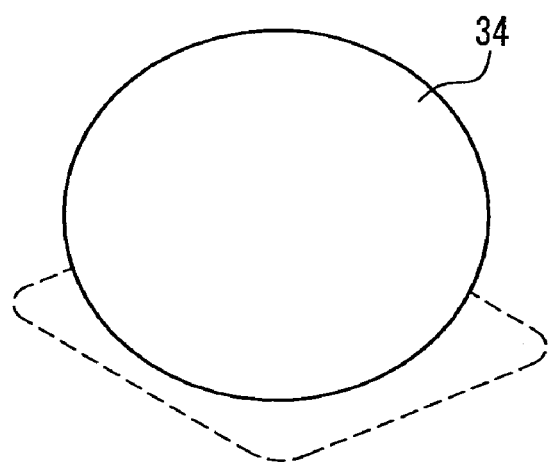
FIG. 8B is a schematic diagram illustrating an X-ray image of defective bonding according to Embodiment 2 of the present invention.

FIGS. 8A and 8B are schematic diagrams illustrating X-ray images of solder balls 4 that were captured at an oblique angle of 45 degrees relative to the plane of the carrier substrate 8, in an orientation furthermore rotated by 45 degrees within the plane of the carrier substrate 8. FIG. 8A is a diagram illustrating satisfactory bonding state of a solder ball 4 with an external connection land 31. FIG. 8B is a diagram illustrating defective bonding state of a solder ball 4 with an external connection land 31. To make the comparison easier, the surface shape of the external connection land 31 is indicated by a broken line. The outer shape of a first solder ball 32 includes straight portions 33. This is because the solder ball 32 wetted and spread over the front surface of the external connection land 31, and the shapes of the straight portions of the external connection land 31 were captured. In other words, the bonding between the solder ball 32 and the external connection land 31 is satisfactory.

On the other hand, the outer shape of a second solder ball 34 is circular without any straight portions. This indicates that the second solder ball 34 did not wet and spread over the external connection land 31, from which it can be determined that the connection between the second solder ball 34 and the external connection land 31 is defective.

Accordingly, by forming such external connection lands 31, the acceptability of the connection state between the solder balls and the external connection lands 31 can be determined easily by whether or not the shape of a solder ball includes a straight portion.

Figure 9A:
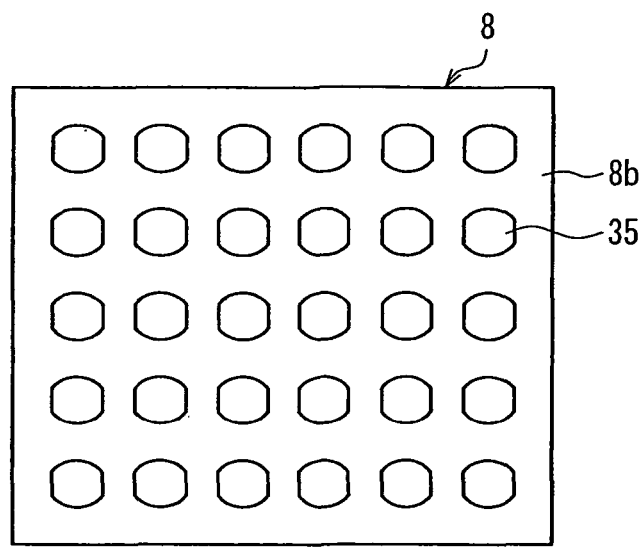
FIG. 9A is a conceptual diagram of the lower surface of another carrier substrate according to Embodiment 2 of the present invention.
Figure 9B:
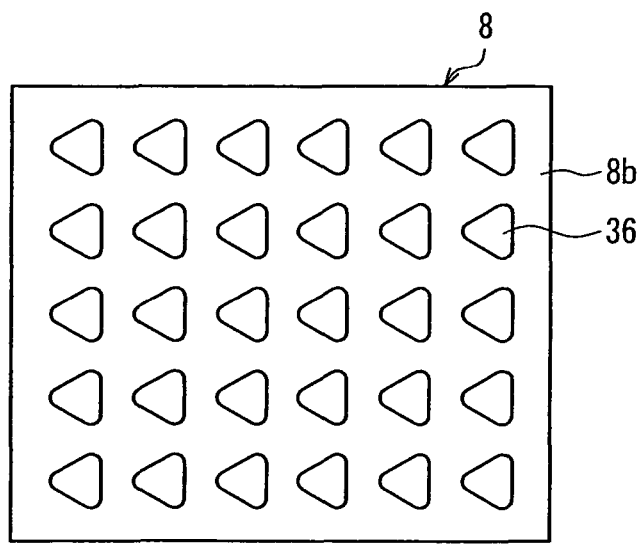
FIG. 9B is a conceptual diagram of the lower surface of another carrier substrate according to Embodiment 2 of the present invention.
Figure 9C:
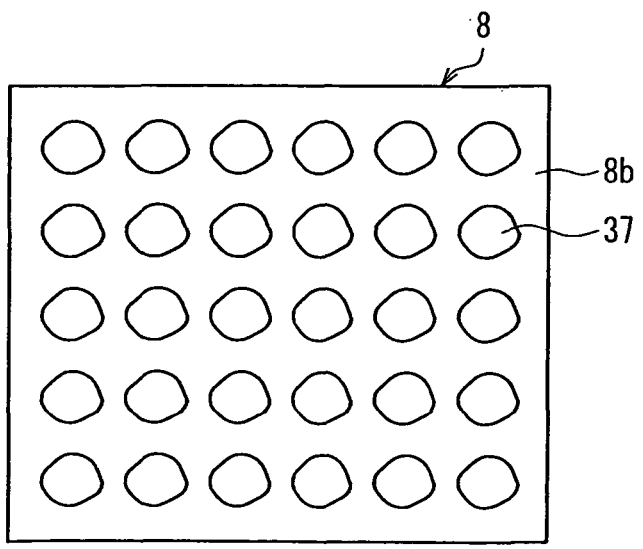
FIG. 9C is a conceptual diagram of the lower surface of another carrier substrate according to Embodiment 2 of the present invention.

The shape of the external connection lands 31 is not limited to the above-described shape, and, for example, external connection lands as shown in FIGS. 9A to 9C may be employed. External connection lands 35 shown in FIG. 9A include two arc portions and two straight portions that connect the ends of the arc portions. External connection lands 36 shown in FIG. 9B have a shape that includes three arc portions serving as the corners of a triangle and three straight portions that connect the ends of the arc portions. External connection lands 37 shown in FIG. 9C have a shape that includes four arc portions and four straight portions that connect the ends of the arc portions. Similar effects can be obtained even when external connection lands other than those described above are formed as long as the external connection lands have a shape including an arc portion and a straight portion.

In the present embodiment, the external connection lands have been described, but by adopting the same configuration in the circuit board-side lands, the occurrence of bonding failures with solder balls can be reduced, and connection reliability can be improved, and at the same time, bondability can be determined easily.

Embodiment 3

Figure 10:
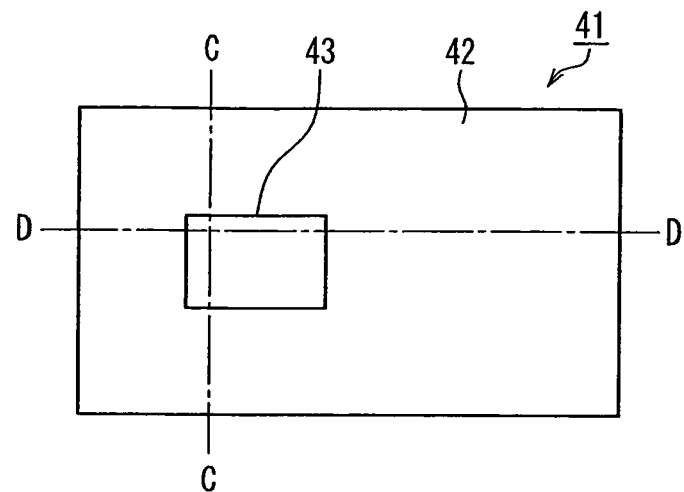
FIG. 10 is a plan view illustrating the configuration of a surface-mount type device mounted structure according to Embodiment 3 of the present invention.

FIG. 10 is a plan view illustrating the configuration of an electronic component mounted apparatus 41 according to Embodiment 3 of the present invention. The electronic component mounted apparatus 41 includes an electronic component package 43 mounted on a circuit board 42. The circuit board 42 includes an insulating substrate made of an epoxy resin or the like, wirings (not shown) that are provided on the insulating substrate, and a resist that is disposed on the wirings and the circuit board 42. The wirings are made of copper or the like. Circuit board-side lands (not shown in FIG. 10) for connecting to the electronic component package 43 are formed on the end portion of the wirings.

The electronic component package 43 is a surface-mount type IC package that includes connection terminals for electrically connecting to the circuit board 42 that are provided in the bottom, and is packaged by, for example, BGA type or LGA type including a carrier substrate or the like CSP. Solder balls are provided on external connection lands that are formed in the electronic component package 43. The solder balls electrically connect the external connection lands and the lands formed on the circuit board 42.

Figure 11:
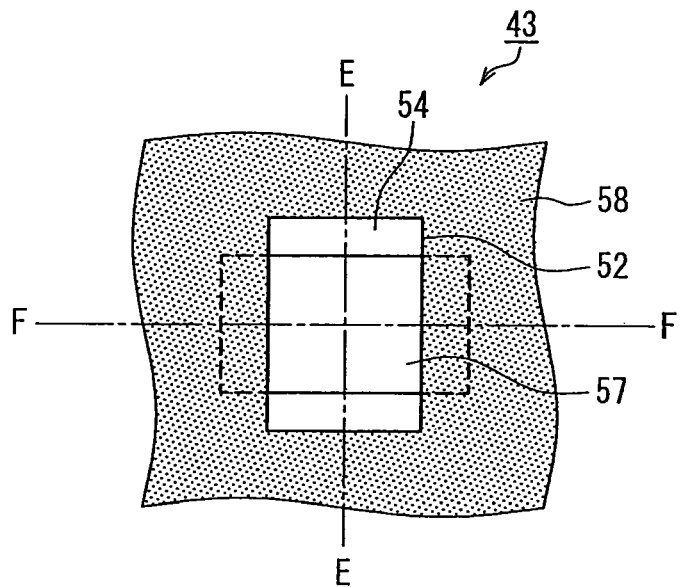
FIG. 11 is a plan view illustrating the configuration of a region of an electronic component package according to Embodiment 3 of the present invention in which a land is disposed.
Figure 12:
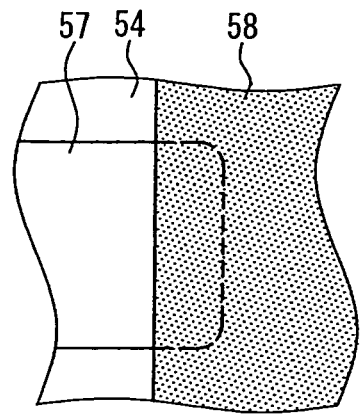
FIG. 12 is an enlarged view showing a part of FIG. 11.

FIG. 11 is a plan view illustrating the configuration of a region of the electronic component package 43 in which an external connection land 57 is disposed. The external connection land 57 is formed to be rectangular. The external connection land 57 is formed by forming a copper foil on the insulating substrate, followed by patterning through wet etching. Accordingly, when viewed closely, the corner portions of the rectangle are arc-shaped as shown in FIG. 12. A rectangular opening 52 is formed in the resist 58.

As shown in FIG. 11, a part of the external connection land 57 is exposed through the opening 52 of the resist 58. The longitudinal direction of the external connection land 57 is orthogonal to the longitudinal direction of the opening 52 of the resist 58. Accordingly, two end portions of the external connection land 57 in the longitudinal direction are covered with the resist 58. In other words, four corners of the external connection land 57 are covered with the resist 58. On the other hand, in the transverse direction of the external connection land 57, the external connection land 57 is free from the resist 58, creating a gap (clearance) 54 between the resist 58 and the external connection land 57.

Figure 13:
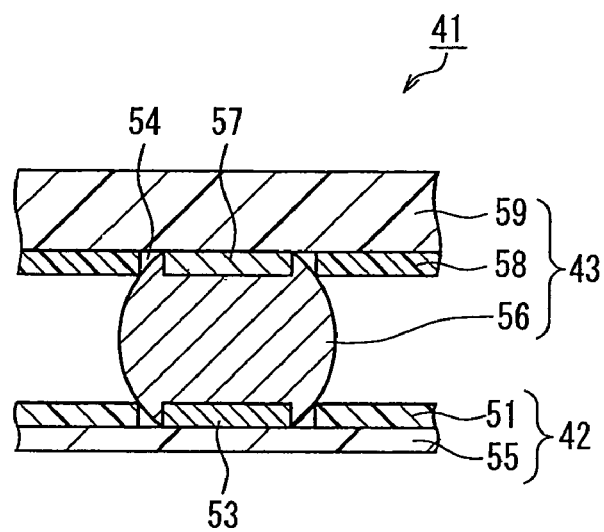
FIG. 13 is a cross-sectional view of the surface-mount type device mounted structure of FIG. 10, taken along line C-C.

FIG. 13 is an enlarged cross-sectional view of a part of the electronic component mounted apparatus 41 of FIG. 10, taken along the C-C line. FIG. 13 also corresponds to the cross section of the external connection land 57 of FIG. 11, taken along the E-E line. A resist 51 and a circuit board-side land 53 are disposed on an insulating substrate 55. The insulating substrate 55 may be multilayered. If the insulating substrate 55 is multilayered, the circuit board-side land 53 is connected to, for example, a via (not shown) that is formed in the insulating substrate 55, and is connected to a wiring of an internal layer of the insulating substrate 55.

The resist 51 is formed to prevent a wiring provided on the surface of the insulating substrate 55 from oxidation and to secure insulation of the wiring from other components. As the resist 51, a solder resist can be used. The electronic component package 43 includes an external connection land 57, a resist 58 disposed in a region of the mounting plane except for where the external connection land 57 is formed, an electronic component 59 and a solder ball 56. The circuit board-side land 53 and the external connection land 57 are connected by the solder ball 56.

The shapes of the resist 51 and the circuit board-side land 53 and their positional relationship are the same as those of the resist 58 and the external connection land 57, and thus their descriptions are omitted.

In FIG. 13, a gap 54 as shown in FIG. 11 is formed between the external connection land 57 and the resist 58. Accordingly, part of the solder ball 56 flows into the gap 54, spreads to the side face of the external connection land 57, and the bonding strength between the external connection land 57 and the solder ball 56 is improved by the anchor effect.

Figure 14:
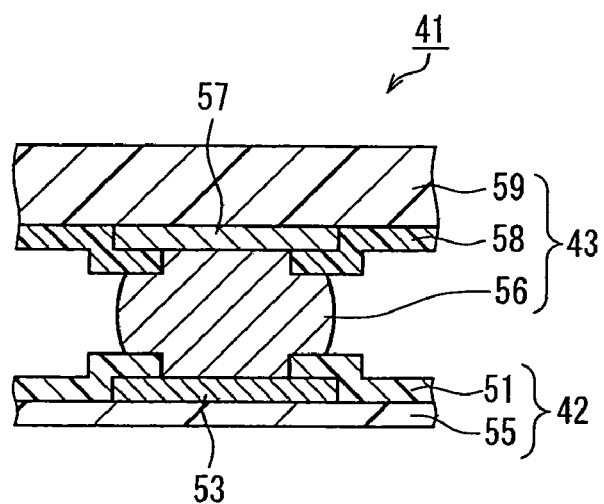
FIG. 14 is a cross-sectional view of the surface-mount type device mounted structure of FIG. 10, taken along line D-D.

FIG. 14 is an enlarged cross-sectional view of a part of the electronic component mounted apparatus 41 of FIG. 10, taken along the D-D line. FIG. 14 also corresponds to the cross section of the external connection land 57 of FIG. 11, taken along the F-F line. In FIG. 14, the resist 58 is disposed such that it partially covers the external connection land 57 as shown in FIG. 11. Specifically, the resist 58 covers four corners of the external connection land 57. This improves the bonding strength between the external connection land 57 and the electronic component 59, and thus makes it difficult for the external connection land 57 to separate from the electronic component 59.

As described above, the electronic component mounted apparatus 41 according to the present embodiment employs a configuration in which a gap 54 is formed between the external connection land 57 and the resist 58 in one direction, and the edge portions of the external connection land 57 are covered with the resist 58 in another direction. Therefore, it is possible to increase both the bonding strength between the external connection land 57 and the solder ball 56 and the bonding strength between the external connection land 57 and the electronic component 59 to such a degree that separation does not occur.

The bonding state between a solder ball 56 and an external connection land 57 of the electronic component mounted apparatus 41 will be described next. When bonding the solder ball 56 and the external connection land 57, the solder ball 56 flows into the gap 54 in the direction of the C-C line of FIG. 10, and bonds firmly to the external connection land 57 by the anchor effect. On the other hand, in the direction of the D-D line of FIG. 10, because the shape of the opening of the resist 58 includes straight portions as shown in FIG. 11, the shape of the bonding portion between the solder ball 56 and the external connection land 57 includes straight portions. In other words, if the bonding is satisfactory, the straight portions appear in an X-ray image of the bonding portion between the solder ball 56 and the external connection land 57. Accordingly, the bonding state between the solder ball 56 and the external connection land 57 can be inspected using the method of inspecting a bonding state between a solder ball and a land described in Embodiment 1.

Also for the circuit board-side land 53, both the bonding strength with the solder ball 56 and the bonding strength with the electronic component 59 can be increased to such a degree that separation does not occur, in the same manner as for the external connection land 57. The bonding state between the solder ball 56 and the circuit board-side land 53 can be inspected using the method of inspecting a bonding state between a solder ball and a land described in Embodiment 1.

Embodiment 4

Figure 15:
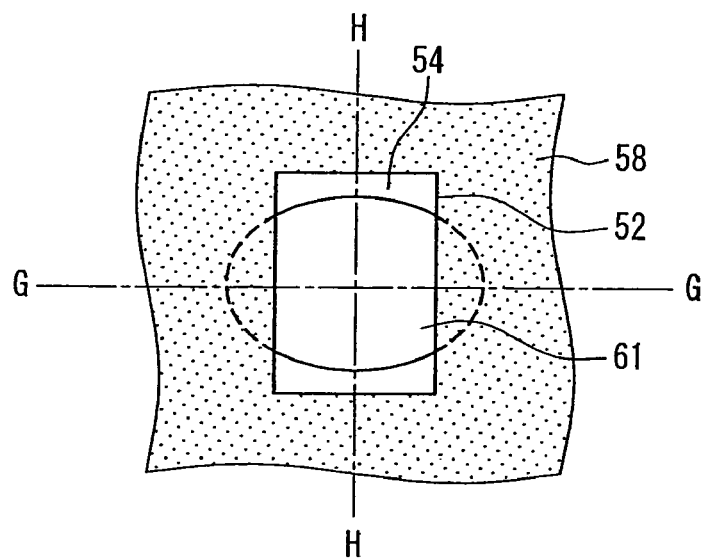
FIG. 15 is a plan view illustrating the configuration of a region of a surface-mount type device mounted structure according to Embodiment 4 of the present invention in which a land is disposed.

FIG. 15 is a plan view illustrating the configuration of a region, in which an external connection land 61 is disposed, of an electronic component mounted apparatus according to Embodiment 4 of the present invention. The present embodiment employs the same configuration as that of Embodiment 3, except that the external connection land 57 of Embodiment 3 is replaced by the elliptic external connection land 61. Because the shapes of the circuit board-side resist 51 and the circuit board-side land 53 and their positional relationship are the same as those of the resist 58 and the external connection land 61, thus their descriptions are omitted. Further, in the present embodiment, the same reference numerals are assigned to elements having the same configuration as those of Embodiment 3, and thus their descriptions are omitted.

The external connection land 61 has an elliptic shape, and is disposed such that its longitudinal direction (the direction of the G-G line) is orthogonal to the longitudinal direction (the direction of the H-H line) of the opening 52. The cross section of the electronic component mounted apparatus taken along the H-H line has the same configuration as that of FIG. 13, except that the external connection land 57 is replaced by the external connection land 61, and a gap 54 is formed between the external connection land 61 and the resist 58. With this configuration, the bonding strength between the external connection land 61 and the solder ball 56 is improved by the anchor effect.

The cross section of the electronic component mounted apparatus taken along the G-G line has the same configuration as that of FIG. 14, except that the external connection land 57 is replaced by the external connection land 61, and the external connection land 61 is covered with the resist 58. This improves the bonding strength between the external connection land 61 and the electronic component 59, and makes it difficult for the external connection land 61 to separate from the electronic component 59.

As described above, the electronic component mounted apparatus according to the present embodiment employs a configuration in which a gap 54 is formed between the external connection land 61 and the resist 58 in one direction, and the edge portions of the external connection land 61 in its longitudinal direction is covered with the resist 58. This can increase both the bonding strength between the external connection land 61 and the solder ball 56 and the bondability between the external connection land 61 and the electronic component 59 to such a degree that separation does not occur.

The bonding state between the solder ball 56 and the external connection land 61 will be described next. When bonding the solder ball 56 and the external connection land 61, the solder ball 56 flows into the gap 54 in the direction of the H-H line of FIG. 15, and bonds firmly to the external connection land 61 by the anchor effect. On the other hand, in the direction of the G-G line of FIG. 15, because the shape of the opening of the resist 58 includes straight portions, the shape of the bonding portion of the solder ball 56 with the external connection land 61 includes straight portions. In other words, if the bonding is satisfactory, the straight portions appear in an X-ray image of the bonding portion between the solder ball 56 and the external connection land 61. Accordingly, the bonding state between the solder ball 56 and the external connection land 61 can be inspected in the same manner as in Embodiment 1.

In the present embodiment, an example has been shown in which the shape of the external connection land 61 is elliptic and the shape of the opening 52 of the resist 58 is rectangular. However, it is also possible to employ a configuration in which the external connection land 61 has a rectangular shape, and the opening 52 of the resist 56 has an elliptic shape.

In Embodiments 3 and 4, the configuration in which the opening of the resist is rectangular has been shown, but the present invention is not limited thereto, and the opening of the resist may be elliptic or square. Similarly, the land shape may be rectangular or elliptic. In other words, as long as the land is disposed on the opening of the resist such that a gap is formed between the land and the resist in one direction, the edge portions of the land is covered with the resist in another direction, and a portion of the land exposed through the opening includes a straight portion, the above-described effects can be obtained.

Similarly, for the circuit board-side land, both the bonding strength with the solder ball 56 and that with the electronic component 59 can be increased to such a degree that separation does not occur, in the same manner as for the external connection land 61. The bonding state between the solder ball 56 and the circuit board-side land can be inspected using the method of inspecting a bonding state between a solder ball and a land described in Embodiment 1.

Embodiment 3 has been described for the case where the position of the gap in the circuit board-side land and the position of the gap in the external connection land are in the same direction. However, the present invention is not limited thereto, and it is possible to configure such that they are located in different directions.

Figure 16:
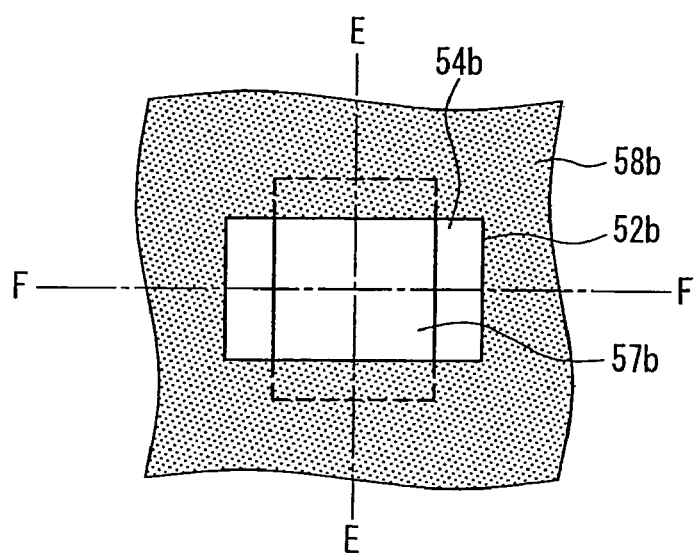
FIG. 16 is a plan view illustrating the configuration of a region in which an external connection land is disposed according to an embodiment of the present invention.
Figure 17:
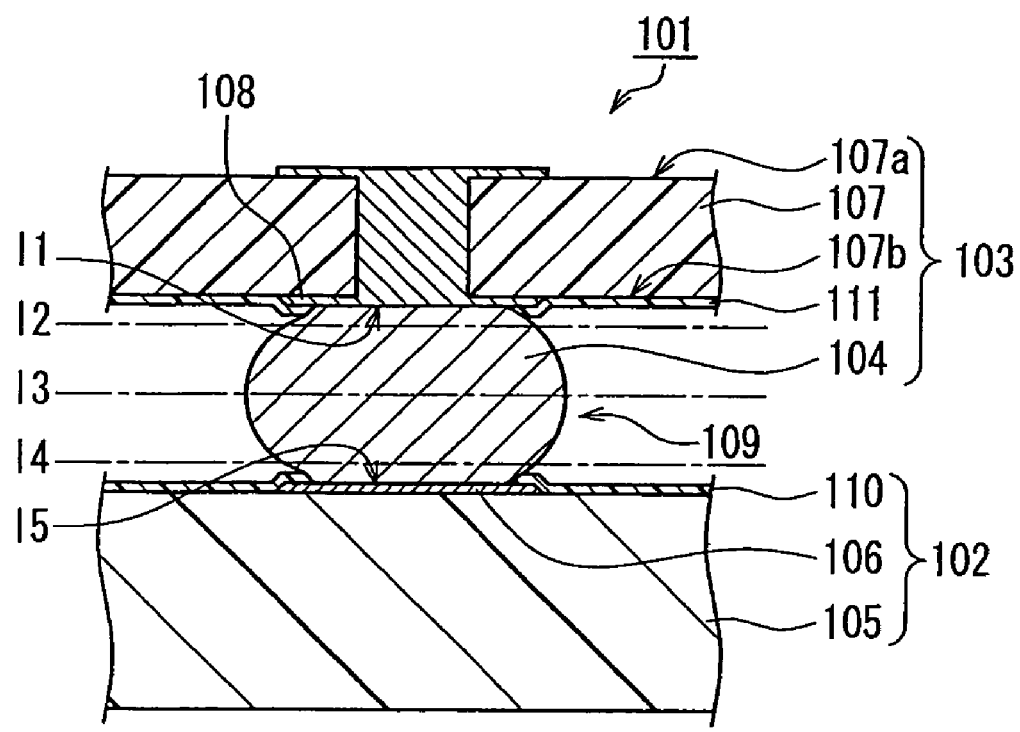
FIG. 17 is a cross-sectional conceptual diagram illustrating the configuration of a conventional electronic component mounted apparatus that includes an electronic component package.
Figure 18:
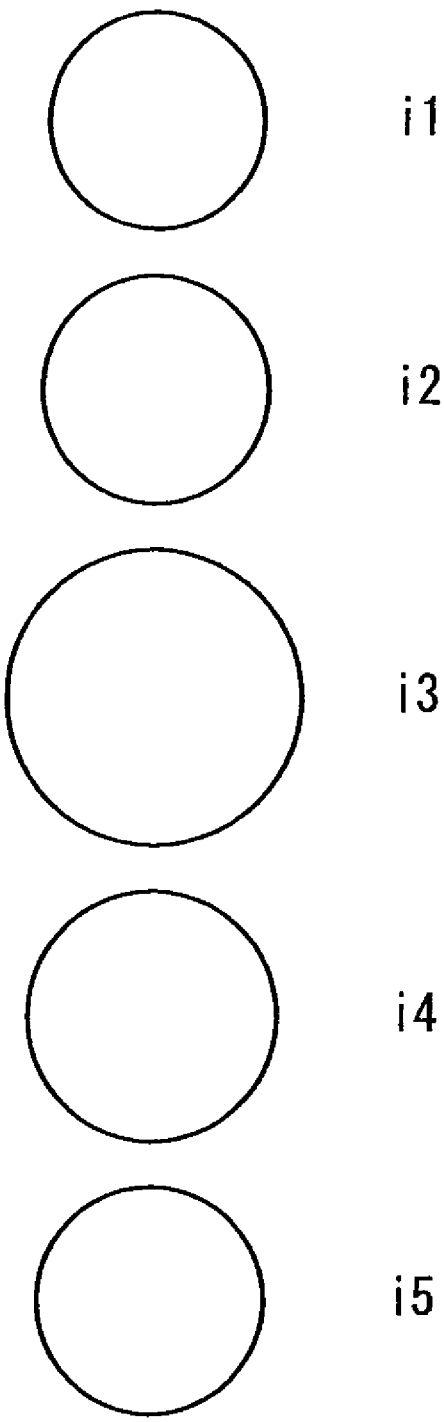
FIG. 18 is a conceptual diagram illustrating the cross sections of slicing planes I1 to I5 of FIG. 17.

FIG. 16 is a plan view illustrating the configuration of a region in which an external connection land 57*b* is disposed. The configuration of a region in which a circuit board-side land is disposed, on which this electronic component mounted apparatus is to be mounted, is the same as that of the region shown in FIG. 11 in which an external connection land is disposed. As shown in FIG. 16, a gap 54*b* is formed in the external connection land 57*b* in the F-F direction. On the other hand, in FIG. 11, a gap is formed in the circuit board-side land in the E-E direction. In other words, the direction of the position of the gap in the electronic component package-side land and that of the gap in the circuit board-side land are orthogonal to each other.

This electronic component mounted apparatus also employs a configuration in which a gap 54*b* is formed between the external connection land 57*b* and the resist 58*b* in one direction as shown in FIG. 16, and the edge portions of the external connection land 57*b* are covered with the resist 58*b* in another direction. Accordingly, both the bonding strength between the external connection land 57*b* and a solder ball and that between the external connection land 57*b* and the electronic component 59 can be increased to such a degree that separation does not occur.

In other words, regardless of whether the longitudinal direction of the external connection land 57*b* and the longitudinal direction of the circuit board-side land match or are orthogonal to each other, the bonding strength between the external connection land and the circuit board-side land with solder is high. Also, in the case of the external connection land and circuit board-side land of Embodiment 4, which have an elliptic shape, regardless of whether the longitudinal directions of the lands match or are orthogonal to each other, similar strength is obtained as well.

As long as either of the external connection lands and the circuit board-side lands have the configuration described in any one of Embodiments 1 to 4, the bonding strength can be increased, and the bondability inspection can be performed. Further, in Embodiments 1 to 4, even when the land configuration is different in the external connection land and the circuit board-side land, the bonding strength can be increased, and the bondability inspection can be performed.

The invention may be embodied in other forms without departing from the spirit or essential characteristics thereof. The embodiments disclosed in this application are to be considered in all respects as illustrative and not limiting. The scope of the invention is indicated by the appended claims rather than by the foregoing description, and all changes which come within the meaning and range of equivalency of the claims are intended to be embraced therein.

What is claimed is:

1. An electronic component package comprising:
   an insulating carrier substrate;
   a connection wiring that is provided on one side of the carrier substrate;
   an IC chip that is connected to the connection wiring;
   an external connection land that is disposed on the other side of the carrier substrate and is connected to the connection wiring via a wiring in the carrier substrate; and
   a solder ball that is disposed on the external connection land,
   wherein a region of the external connection land that is bonded to the solder ball has an outer shape that includes at least one arc portion and at least one straight portion, and
   a region of the solder ball that is bonded to the external connection land has an outer shape that includes at least one arc portion and at least one straight portion in accordance with the outer shape of the external connection land.

2. The electronic component package according to claim 1, wherein an entire surface of the external connection land is the region that is bonded to the solder ball.

3. The electronic component package according to claim 1, further comprising a resist that is disposed on the other side of the carrier substrate and has an opening,
   wherein a region of the external connection land that is exposed through the opening of the resist is the region that is bonded to the solder ball.

4. The electronic component package according to claim 1, wherein the region of the external connection land that is bonded to the solder ball has an outer shape that includes a substantially semicircular arc portion and a straight portion that connects two ends of the arc portion.

5. The electronic component package according to claim 1, wherein the region of the external connection land that is bonded to the solder ball has an outer shape that includes a plurality of arc portions and a plurality of straight portions, each of the straight portions connecting one end of an arc portion and one end of another arc portion.

6. A method of inspecting a bonding portion between the external connection land and the solder ball in the electronic component package according to claim 1,
   wherein X-rays are irradiated on the solder ball and it is determined that the bonding portion between the external connection land and the solder ball in the electronic component package is satisfactory if a straight portion is included in the outer shape of the solder ball in an image formed based on X-rays that have passed through the solder ball.

7. The method according to claim 6 for inspecting a bonding portion in the electronic component package, wherein the X-rays are irradiated obliquely relative to a plane of the carrier substrate of the electronic component package.

8. A circuit board comprising:
   an insulating substrate;
   a circuit board-side land that is disposed on the insulating substrate; and
   a wiring that is provided on the insulating substrate and is connected to the circuit board-side land,
   wherein a region of the circuit board-side land that can be bonded to a solder ball of an electronic component package to be mounted has an outer shape that includes at least one arc portion and at least one straight portion, and
   when the region of the circuit board-side land is bonded to the solder ball, a region of the solder ball has an outer shape that includes at least one arc portion and at least one straight portion in accordance with the outer shape of the circuit board-side land.

9. The circuit board according to claim 8, wherein an entire surface of the circuit board-side land is the region that can be bonded to the solder ball of the electronic component package to be mounted.

10. The circuit board according to claim 8, further comprising a resist that is disposed on the insulating substrate and has an opening,
    wherein a region of the circuit board-side land that is exposed through the opening of the resist is a region that can be bonded to the solder ball of the electronic component package to be mounted.

11. The circuit board according to claim 8, wherein the region of the circuit board-side land that can be bonded to the solder ball of the electronic component package to be mounted has an outer shape that includes a substantially semicircular arc portion and a straight portion that connects two ends of the arc portion.

12. The circuit board according to claim 8, wherein the region of the circuit board-side land that can be bonded to the solder ball of the electronic component package to be mounted has an outer shape that includes a plurality of arc portions and a plurality of straight portions, each of the straight portions connecting one end of an arc portion and one end of another arc portion.

13. An electronic component mounted apparatus comprising:
    an electronic component package comprising;
       an insulating carrier substrate;
       a connection wiring that is provided on one side of the carrier substrate;
       an IC chip that is connected to the connection wiring;
       an external connection land that is disposed on the other side of the carrier substrate and is connected to the connection wiring via a wiring in the carrier substrate; and
       a solder ball that is disposed on the external connection land; and
    a circuit board comprising:
       an insulating substrate;
       a circuit board-side land that is disposed on the insulating substrate; and
       a wiring that is provided on the insulating substrate and is connected to the circuit board-side land;
    wherein the solder ball is connected to the circuit board-side land;

a region of the external connection land that is bonded to the solder ball has an outer shape that includes at least one arc portion and at least one straight portion;

a region of the solder ball that is bonded to the external connection land has an outer shape that includes at least one arc portion and at least one straight portion in accordance with the outer shape of the external connection land;

a region of the circuit board-side land that is bonded to the solder ball of the electronic component package has an outer shape that includes at least one arc portion and at least one straight portion; and a region of the solder ball has an outer shape that includes at least one arc portion and at least one straight portion in accordance with the outer shape of the circuit board-side land.

14. A method of inspecting the bonding portion between the external connection land and the circuit board-side land by the solder ball in the electronic component mounted apparatus according to claim 13, wherein X-rays are irradiated on the solder ball and it is determined that at least one of the bonding portion between the external connection land of the electronic component package and the solder ball and the bonding portion between the circuit board-side land of the circuit board and the solder ball is satisfactory if a straight portion is included in the outer shape of the solder ball in an image formed based on X-rays that have passed through the solder ball.

15. The method according to claim 14 for inspecting the bonding portion in the electronic component mounted apparatus, wherein the X-rays are irradiated obliquely relative to a plane of the carrier substrate of the electronic component package.

* * * * *